United States Patent [19]

Goddard

[11] Patent Number: 4,980,275
[45] Date of Patent: Dec. 25, 1990

[54] PHOTOGRAPHIC MATERIAL AND PROCESS COMPRISING A DYE STABILIZER

[75] Inventor: John D. Goddard, The Dell, United Kingdom

[73] Assignee: Eastman Kodak Company, Rochester, N.Y.

[21] Appl. No.: 322,962

[22] Filed: Mar. 13, 1989

[30] Foreign Application Priority Data

Apr. 13, 1988 [GB] United Kingdom ............... 8808694

[51] Int. Cl.$^5$ ............................................. G03C 1/34
[52] U.S. Cl. .................................... 430/551; 430/610; 430/614; 430/372
[58] Field of Search ............... 430/551, 610, 372, 614

[56] References Cited

U.S. PATENT DOCUMENTS

| | | | |
|---|---|---|---|
| 3,057,721 | 10/1962 | Cowden et al. | 430/255 |
| 3,544,336 | 12/1970 | Milton | 430/610 |
| 3,853,592 | 12/1974 | Crawford et al. | 117/60 |
| 4,318,845 | 3/1982 | Spivack et al. | 524/91 |
| 4,326,022 | 4/1982 | Ito et al. | 490/546 |
| 4,346,154 | 8/1982 | McLaen et al. | 430/14 |
| 4,411,985 | 10/1983 | Morrow et al. | 430/352 |
| 4,661,440 | 4/1987 | Tschopp et al. | 430/512 |
| 4,749,645 | 6/1988 | Goddard | 430/551 |

FOREIGN PATENT DOCUMENTS

| | | |
|---|---|---|
| 4832728 | 12/1969 | Japan . |
| 5412820 | 9/1972 | Japan . |
| 5567741 | 11/1978 | Japan . |
| 1066261 | 4/1967 | United Kingdom . |

OTHER PUBLICATIONS

Research Disclosure, Dec. 1978, Item 17643, *Research Disclosure* Kenneth Mason Publications, Hampshire, England.

Research Disclosure, Oct. 1981, Item 21001, *Research Disclosure* Kenneth Mason Publications, Hampshire, England.

*Primary Examiner*—Paul R. Michl
*Assistant Examiner*—Janet C. Baxter
*Attorney, Agent, or Firm*—Richard E. Knapp

[57] ABSTRACT

A photographic silver halide material comprises an organophosphorus dye stabilizer represented by the formula:

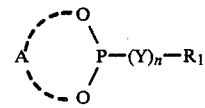

wherein
A represents the atoms necessary to complete a substituted or unsubstituted heterocyclic ring;
$R_1$ represents substituted or unsubstituted alkyl, substituted or unsubstituted cycloalkyl, substituted or unsubstituted alkenyl, substituted or unsubstituted aryl, or a heterocyclic group;
Y is an oxygen or a sulfur atom; and,
n is 0 or 1.

Such a photographic silver halide material enables improved stability of dye images in the material.

11 Claims, No Drawings

PHOTOGRAPHIC MATERIAL AND PROCESS COMPRISING A DYE STABILIZER

The invention relates to a photographic element and process comprising a dye stabilizer. More particularly, it relates to the use of certain organophosphorus compounds as stabilizers for improving the stability of dye images obtained by color developing coupler-incorporated photographic silver halide materials.

A common form of color photographic material comprises red-, green- and blue-sensitive silver halide emulsion layers in or adjacent to which are incorporated cyan-, magenta- and yellow-dye forming couplers, respectively. On development of such a material with a developer containing p-phenylenediamine color developing agent, the oxidation product produced on reduction of the silver halide by the developing agent reacts with the appropriate coupler to give image dye.

The dye image obtained by color development can deteriorate as a result of the action of light, heat and/or humidity and various measures are known for reducing such deterioration.

U.S. Pat. No. 4,326,022 describes the use of high boiling organophosphorus coupler solvents which are said to improve the resistance of developed dye images to such deterioration. While dye stabilization can be achieved in this way, it is desirable to be able to improve dye stability without putting any restriction on the coupler solvent employed.

Japanese Published patent application No. 48 32728 describes the use of certain open chain phosphorus acid esters to improve dye stability in photographic materials. The esters may be liquids or solids.

It has been desirable to provide organophosphorus compounds which can be incorporated in a color photographic material to improve dye stability independently of the coupler solvent used. Unlike the high boiling solvents described in the prior art, it has been desirable to provide such compounds that are solids which can be readily obtained in pure form. Further, it has been desirable to provide compounds that are more resistant to hydrolysis than the open-chain phosphorus acid esters described in the prior art. It has been desirable to provide such compounds that can be prepared easily and at low cost.

It has been found that such advantages are provided by a photographic element comprising a support bearing at least one photographic silver halide emulsion layer and, incorporated in that layer or a water-permeable layer adjacent thereto, a dye-forming coupler, wherein the element contains, incorporated in the coupler containing layer or a water-permeable layer adjacent thereto, an organophosphorus dye stabilizer represented by the formula:

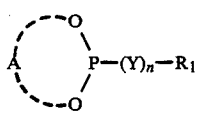

wherein

A represents the atoms necessary to complete a substituted or unsubstituted heterocyclic ring;

$R_1$ represents substituted or unsubstituted alkyl, substituted or unsubstituted cycloalkyl, substituted or unsubstituted alkenyl, substituted or unsubstituted aryl, or a heterocyclic group;

Y is oxygen (O) or sulphur (S); and, n is 0 or 1.

The structural features of the compounds can be chosen to maintain and even improve other desirable characteristics of the photographic system such as dispersion stability, coupling activity, dye hue and emulsion photosensitivity.

A preferred organophosphorus dye stabilizer is represented by the formula:

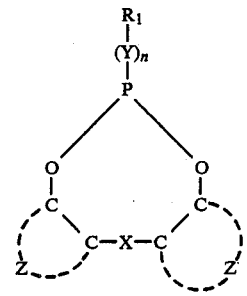

wherein $R_1$, Y and n are as defined above;

each Z independently represents the atoms necessary to complete a substituted or unsubstituted benzene ring; and, X is a single bond or a linking group wherein a single atom separates the benzene rings.

A particularly preferred organophosphorus dye stabilizer has the formula:

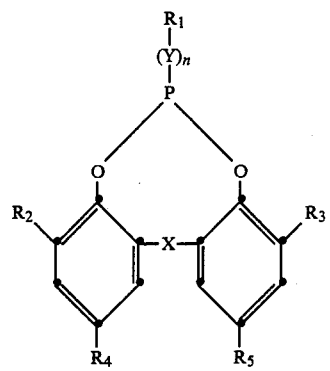

wherein

Y, n, $R_1$ and X are as defined above; and, each of $R_2$, $R_3$, $R_4$ and $R_5$ independently represents hydrogen, substituted or unsubstituted alkyl, substituted or unsubstituted cycloalkyl, substituted or unsubstituted alkenyl, substituted or unsubstituted aryl or a heterocyclic group.

Examples of linking group X include substituted or unsubstituted methylene; substituted or unsubstituted alkylidene, such as butylidene or 3,5,5, trimethylhexylidene; a heteroatom, such as oxygen or sulphur; and sulphonyl.

Preferably, X is $-CR_6R_7-$ in which each of $R_6$ and $R_7$ independently represents hydrogen, substituted or unsubstituted alkyl, substituted or unsubstituted cycloalkyl, substituted or unsubstituted alkenyl, substituted or unsubstituted aryl or a heterocyclic group.

Preferably, at least one of $R_6$ and $R_7$ is hydrogen.

Preferably, $R_2$ and $R_3$ are identical and, independently, $R_4$ and $R_5$ are identical.

Examples of suitable $R_1$ groups include alkyl groups having from 1 to 20 carbon atoms such as methyl, ethyl, propyl, butyl, decyl and heptadecyl; cycloalkyl groups such as cyclohexyl; aryl groups such as phenyl and naphthyl; and heterocyclic groups such as pyrrolidinyl and morpholinyl.

Preferably $R_1$ is a substituted or unsubstituted phenyl group or a substituted or unsubstituted alkyl group.

Specific examples of useful organophosphorus dye stabilizers are as follows:

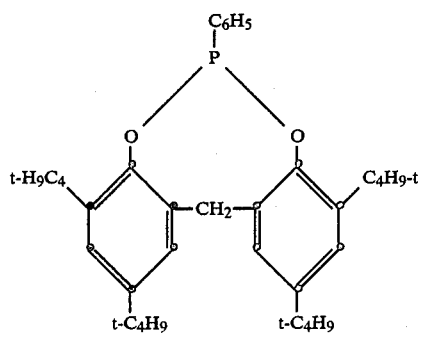

I-1

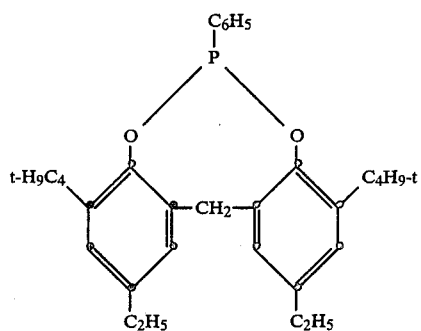

I-2

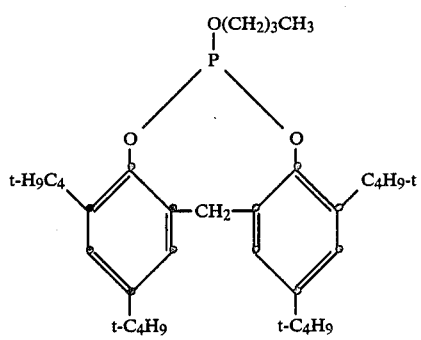

I-3

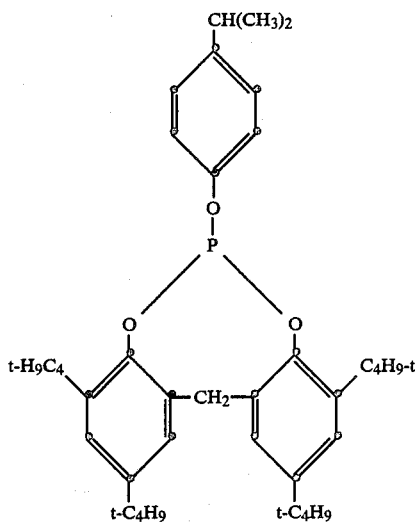

I-4

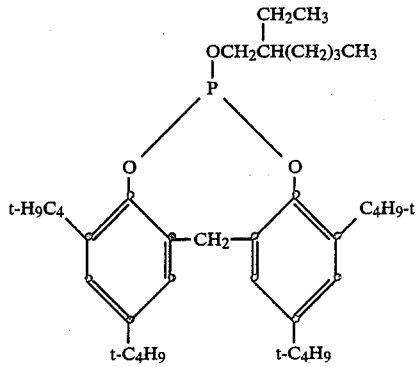

I-5

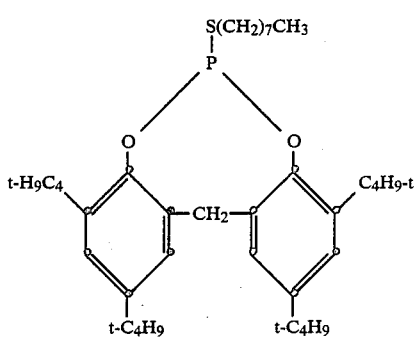

I-6

I-7

-continued
I-8
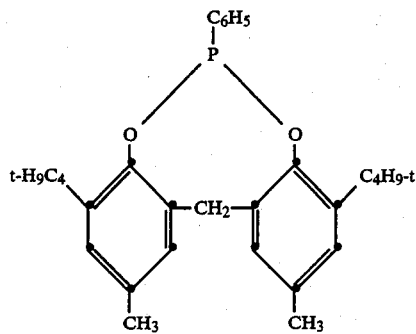
I-9
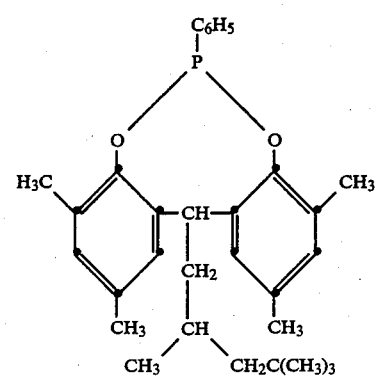
I-10
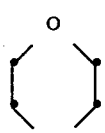
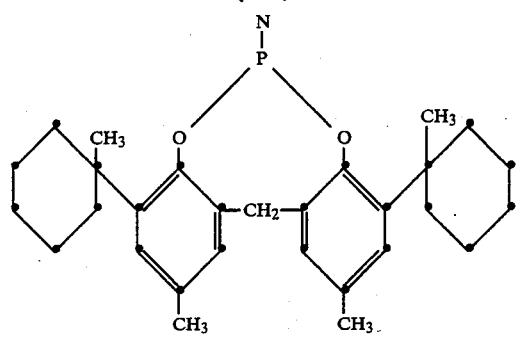
I-11
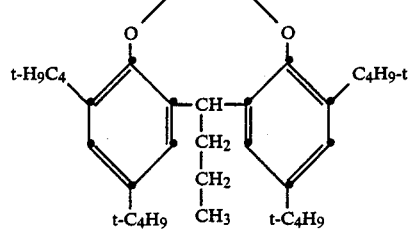
-continued
I-12
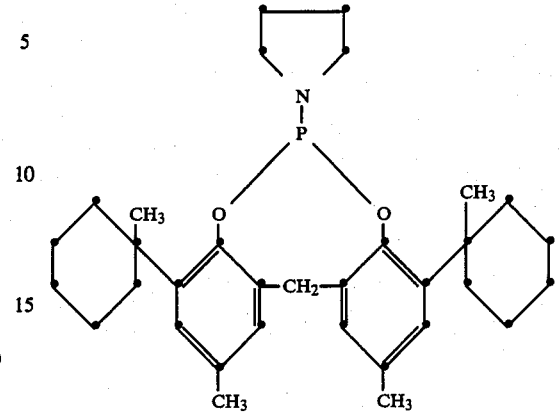
I-13
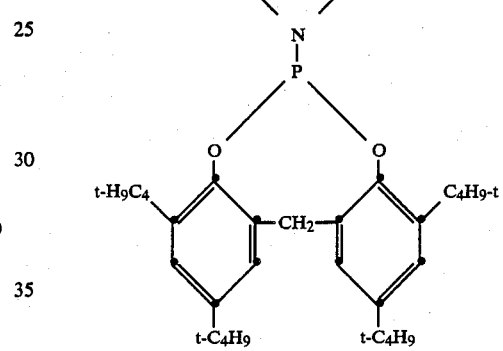
I-14
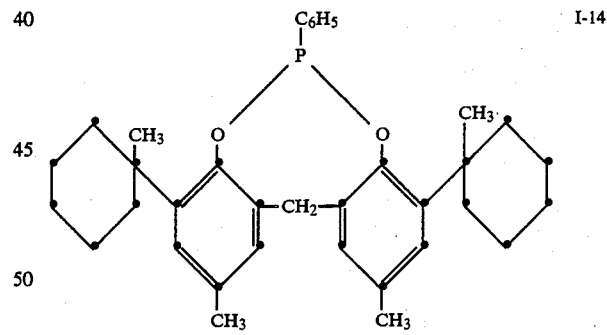
I-15
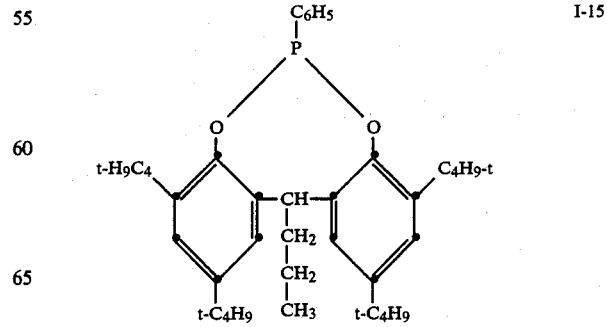
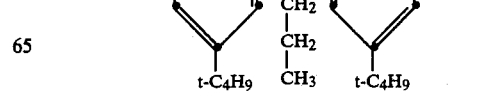

-continued

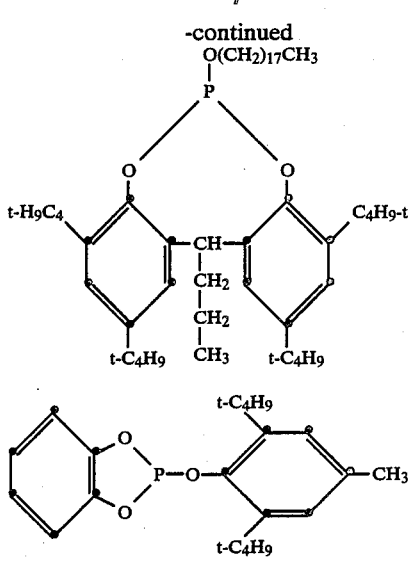

I-16

I-17

The described organophosphorus compounds are readily prepared by reacting an appropriate phosphorus acid chloride with an appropriate phenol or alcohol, usually in the presence of a strong base. Many of these starting materials are commercially available. Thus, for example, the reaction for the preparation of compound I-1 may be represented as follows:

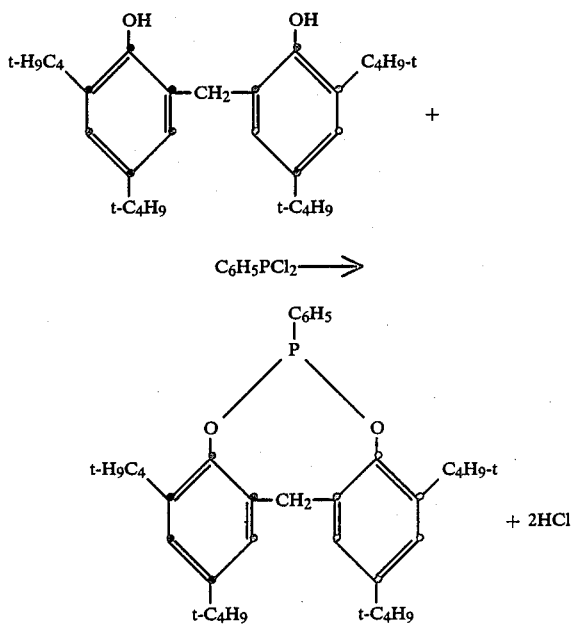

The organophosphorus compounds are used in a concentration sufficient to stabilize the photographic image dyes and their precursors such as in a concentration within the range of 0.1 to 2.0 moles per mole of coupler, more preferably of 0.5 to 1.0 mole per mole of coupler.

The described dye stabilizer must be incorporated in a silver halide emulsion layer or a layer adjacent thereto. It can be incorporated as a separate dispersion, but is preferably incorporated in admixture with the coupler. Both coupler and stabilizer may be dissolved in a conventional coupler solvent, such as dibutyl phthalate. As in the production of ordinary coupler dispersions, a volatile and/or water-miscible auxiliary solvent, such as ethyl acetate, may be used to aid the dispersion process and then removed by evaporation or by washing the set dispersion. Also, the dispersion process can be assisted by the presence of a surface active compound, as usual in the manufacture of coupler dispersions.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K., the disclosures of which are incorporated herein by reference. This publication will be identified hereafter as "Research Disclosure". References giving information on couplers and on methods for their dispersions are given in Sections VII and XIV, respectively, of Research Disclosure.

The couplers commonly employed in photographic materials are useful in photographic elements and processes of the invention. Such couplers typically are water-insoluble compounds often containing ballast groups, phenolic (including naphtholic) couplers being used for producing cyan dyes and compounds containing an activated methylene group, including both heterocyclic and open-chain compounds, being used for producing magenta and yellow dyes. Important magenta couplers are pyrazolones and important yellow couplers are benzoylacetanilides. Couplers that are useful include, for example, those described in the following U.S. Pat. Nos.:

| Cyan Dye-Forming | |
|---|---|
| 3,367,531 | 3,034,892 |
| 2,423,730 | 3,311,476 |
| 2,474,730 | 3,419,390 |
| 2,772,826 | 3,458,315 |
| 2,895,826 | 3,476,563 |
| | 4,339,999 |
| Megenta Dye-Forming | |
| 2,343,703 | 3,062,653 |
| 2,369,489 | 3,127,269 |
| 2,600,788 | 3,311,476 |
| 2,908,573 | 3,419,391 |
| 2,933,391 | 3,518,429 |
| Yellow Dye-Forming | |
| 2,298,443 | 3,277,155 |
| 2,407,210 | 3,408,194 |
| 2,875,057 | 3,415,652 |
| 2,908,573 | 3,447,928 |
| 3,265,506 | 3,993,501 |

An account of dye-forming development is given in 'Modern Photographic Processing', Vol. 2, Grant Haist, Wiley, New York, 1978, Chapter 9.

The dye stabilizers are useful in any coupler-incorporated silver halide photographic materials, including monochrome materials, false-color materials and color transparency, negative and print materials, to stabilize the image dye obtained on development with a solution including a p-phenylenediamine color developing agent. Such developing agents are well known, being described in, for example *Photographic Processing Chemistry*, L. F. A. Mason, Focal Press, London, 2nd edition (1975) pp 229–235 and *Modern PHotographic Processing*, Grant Haist, Wiley, New York (1979), Volume 2 pp 463-8.

The silver halide emulsion employed in the elements of this invention can be either negative working or positive working. Suitable emulsions and their preparation are described in Research Disclosure Sections 1 and II and the publications cited therein. Suitable vehicles for the emulsion layers and other layers of elements of this invention are described in Research Disclosure Section IX and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section X), coating aids (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

An example of the preparation of a stabilizer compound used in the present invention is as follows:

Preparation of
2,4,8,10-Tetra-t-butyl-6-phenyl-12H-dibenzo(d,g)-(1,3,2)-dioxaphosphocin (Compound I-1)

2,2'-Methylenebis(2,4-di-t-butylphenol) (84.93 g, 0.2 mole) and triethylamine (50 g) were dissolved in dry toluene (500 ml). Dichlorophenylphosphine (34.58 g, 0.2 mole) was added dropwise at around 5° C. The reaction mixture was stirred overnight at room temperature and extracted with dilute hydrochloric acid. The organic layer was dried over magnesium sulphate, evaporated under vacuum and the residue recrystallized from ethyl acetate.

Yield=81%, m.p. of pure product=207°-209° C.

Compounds I-2 to I-17 were prepared in an analogous manner.

All the compounds prepared were fully characterized by elemental analysis, nuclear magnetic resonance, thin layer chromatography, high performance liquid chromatography and melting point.

The invention is further illustrated in the following Examples.

EXAMPLE 1

Single layer strips were prepared by coating gelatin subbed polyethylene coated paper supports or polyethyleneterephthalate supports with a photosensitive layer containing a silver bromoiodide emulsion at 0.38 g Ag m$^{-2}$, gelatin at 1.36 g m$^{-2}$ and a dispersion of the yellow image Coupler I in dibutyl phthalate as the coupler solvent (1.5 moles per mole of coupler) and Compound I-1 (0.5 mole per mole of coupler). The coupler coverage was 0.83 millimoles m$^{-2}$. The photographic layer was overcoated with a layer containing gelatin at 3.0 g m$^{-2}$ and bis-vinylsulphonylmethyl ether hardener at 1.0 weight percent based on total gelatin. Control coatings were prepared in the same way except that Compound I-1 was omitted.

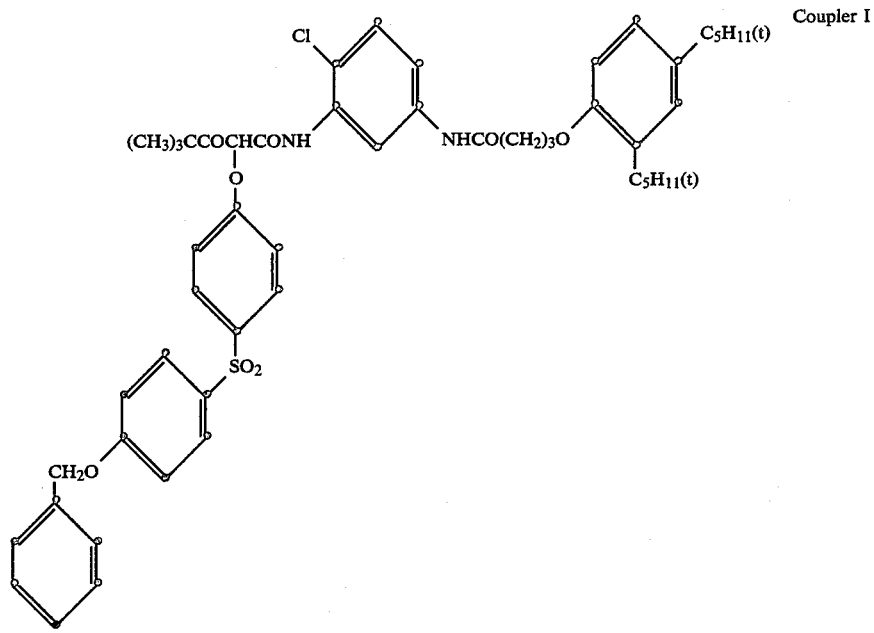

Coupler I

Samples were exposed through a graduated density test object and developed using a standard Ektaprint-2 process (see British Journal of Photography Annual 1986, pages 37 and 38). The processed strips were faded using a 5.4 Klux xenon light source, the ultraviolet component of which was removed using a filter consisting of a coating of Tinuvin 328 (Tinuvin 328 is a Trademark of Ciba-Geigy, Switzerland) (750 mg m$^2$) is a gelatin dispersion, on a polyester support. Table 1 shows the relevant data.

TABLE 1

| Coating | Stabilizer | Fade Time | Density | % Fade |
|---|---|---|---|---|
| Control | — | — | 1.07 | — |
| Control | — | 168 hr. | 0.85 | 21 |
| Control | — | 360 hr. | 0.53 | 51 |
| Example 1 | I-1 | — | 1.01 | — |
| Example 1 | I-1 | 168 hr. | 0.92 | 9 |
| Example 1 | I-1 | 360 hr. | 0.82 | 19 |

The results show that the presence of the organophosphorus compound considerably improved the stability of the yellow image dye.

EXAMPLES 2 to 4

The procedure of Example 1 was repeated using different stabilizer compounds. Fading was measured after a period of six weeks for each of the coatings produced. The results are shown in Table 2.

TABLE 2

| Coating | Stabilizer | % Fade |
|---|---|---|
| Control | — | 15 |
| Example 2 | I-4 | 6 |
| Example 3 | I-5 | 5 |
| Example 4 | I-3 | 2 |

The results show that the presence of the organophosphorus compound improved dye stability.

The invention has been described in detail with particular reference to preferred embodiments thereof, but it will be understood that variations and modifications can be effected within the spirit and scope of the invention.

What is claimed is:

1. A photographic element comprising a support bearing at least one photographic silver halide emulsion layer, a dye-forming coupler and an organophosphorus dye stabilizer represented by the formula:

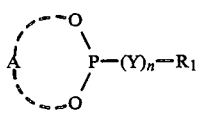

wherein
  A represents the atoms necessary to complete a substituted or unsubstituted heterocyclic ring;
  R$_1$ represents substituted or unsubstituted alkyl, substituted or unsubstituted cycloalkyl, substituted or unsubstituted alkenyl, substituted or unsubstituted aryl, or a heterocyclic group;
  Y is an oxygen or a sulfur atom; and,
  n is 0 or 1.

2. A photographic element as in claim 1, wherein the organophosphorus dye stabilizer is represented by the formula:

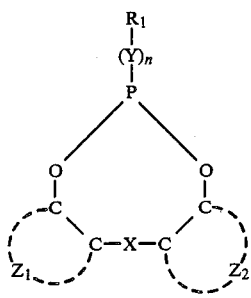

wherein $R_1$ represents substituted or unsubstituted alkyl, substituted or unsubstituted cycloalkyl, substituted or unsubstituted alkenyl, substituted or unsubstituted aryl, or a heterocyclic group;

Y is oxygen or sulfur; and n is 0 or 1;

each of $Z_1$ and $Z_2$ independently represents the atoms necessary to complete an optionally substituted benzene ring; and, X is a single bond or a linking group wherein a single atom separates the benzene rings.

3. A photographic element as in claim 2, wherein the organophosphorus compound has the formula

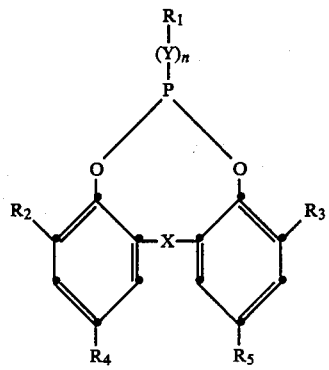

wherein $R_1$ represents substituted or unsubstituted alkyl, substituted or unsubstituted cycloalkyl, substituted or unsubstituted alkenyl, substituted or unsubstituted aryl, or a heterocyclic group;

Y is oxygen or sulfur;

n is 0 or 1;

X is a single bond or a linking group wherein a single atom separates the benzene rings;

each of $R_2$, $R_3$, $R_4$ and $R_5$ independently represents hydrogen, substituted or unsubstituted alkyl, substituted or unsubstituted cycloalkyl, substituted or unsubstituted alkenyl, substituted or unsubstituted aryl or a heterocyclic group.

4. A photographic element as in claim 2, wherein X is substituted or unsubstituted methylene; substituted or unsubstituted alkylidene; a heteroatom; or sulphonyl.

5. A photographic element as in claim 2, wherein X is $-CR_6R_7-$ in which each of $R_6$ and $R_7$ independently represents hydrogen, substituted or unsubstituted alkyl, substituted or unsubstituted cycloalkyl, substituted or unsubstituted alkenyl, substituted or unsubstituted aryl or a heterocyclic 6. A photographic element as in claim 3, wherein $R_2$ and $R_3$ are identical and, independently, $R_4$ and $R5$ are identical.

7. A photographic element as in claim 1, wherein $R_1$ is a substituted or unsubstituted phenyl group or a substituted or unsubstituted alkyl group.

8. A photographic element as in claim 1, wherein the organophosphorus dye stabilizer is present in an amount from 0.1 to 2.0 moles per mole of coupler.

9. A photographic element as in claim 1, wherein the organophosphorus dye stabilizer is contained in one or more layers of a multilayer, multicolor photographic element.

10. A process of forming a color photographic image that comprises developing an exposed silver halide photographic element comprising a coupler that yields a dye image, in the presence of an organophosphorus dye stabilizer as defined in claim 1.

11. A photographic element comprising a support bearing at least one photographic silver halide emulsion layer, a dye-forming coupler and an organophosphorus dye stabilizer that is

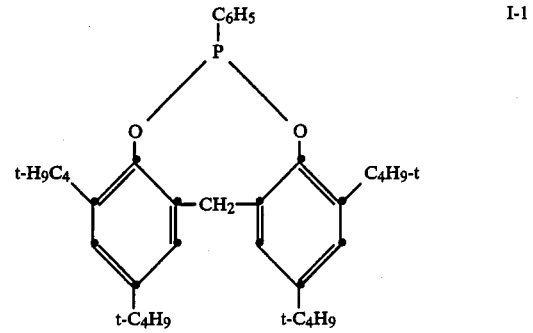

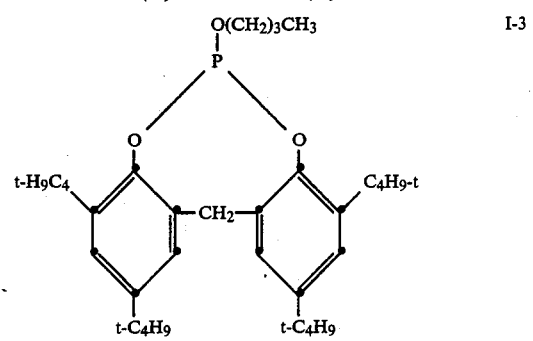

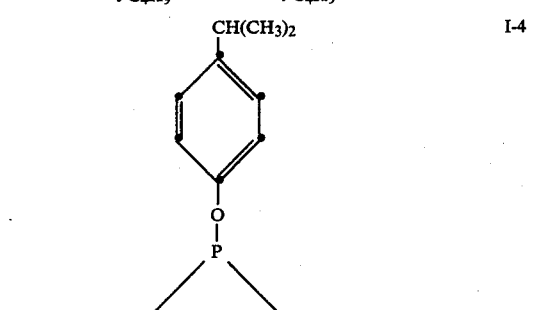

or

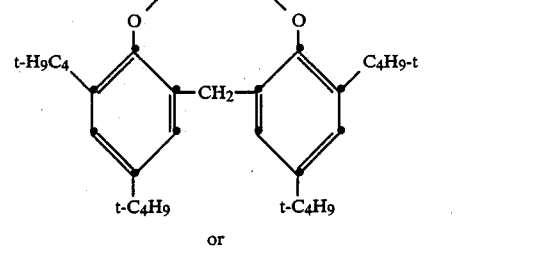

* * * * *

UNITED STATES PATENT AND TRADEMARK OFFICE
CERTIFICATE OF CORRECTION

PATENT NO. : 4,980,275
DATED : December 25, 1990
INVENTOR(S) : John D. Goddard

It is certified that error appears in the above-indentified patent and that said Letters Patent is hereby corrected as shown below:

(1) Title Page, first column, item [30], line 2, "8808694" should read --8808694.7--.

(2) Title Page, first column, under FOREIGN PATENT DOCUMENTS, first line, "4832728" should read --48-32728--.

(3) Title Page, first column, under FOREIGN PATENT DOCUMENTS, second line, "5412820" should read --54-12820--.

(4) Title Page, first column, under FOREIGN PATENT DOCUMENTS, third line, "5567741" should read --55-67741--

(5) Column 1, line 52, "adJacent" should read --adjacent--.

(6) Column 2, line 34, "haS" should read --has--.

(7) Column 8, line 38, "2,474,730" should read --2,474,293--.

UNITED STATES PATENT AND TRADEMARK OFFICE
CERTIFICATE OF CORRECTION

PATENT NO. : 4,980,275
DATED : December 25, 1990
INVENTOR(S) : John D. Goddard

It is certified that error appears in the above-indentified patent and that said Letters Patent is hereby corrected as shown below:

(8) Column 8, line 66, "PHotographic" should read --Photographic--.

(10) Column 13, line 52, "heterocyclic" should read --heterocyclic group.--.

Signed and Sealed this

Fourteenth Day of September, 1993

Attest:

BRUCE LEHMAN

Attesting Officer

Commissioner of Patents and Trademarks